(12) United States Patent
Schrenzel et al.

(10) Patent No.: US 7,955,796 B2
(45) Date of Patent: Jun. 7, 2011

(54) **METHOD FOR THE DIRECT DETECTION OF METHICILLIN-RESISTANT *STAPHYLOCOCCUS AUREUS***

(75) Inventors: Jacques Schrenzel, Geneva (CH); Patrice Francois, Cran-Gevrier (FR)

(73) Assignee: Jacques Schrenzel, Geneva (CH)

( * ) Notice: Subject to any disclaimer, the term of this patent is extended or adjusted under 35 U.S.C. 154(b) by 105 days.

(21) Appl. No.: 10/471,819

(22) PCT Filed: Mar. 14, 2002

(86) PCT No.: PCT/EP02/02897
§ 371 (c)(1),
(2), (4) Date: Jan. 7, 2004

(87) PCT Pub. No.: WO02/082086
PCT Pub. Date: Oct. 17, 2002

(65) Prior Publication Data
US 2004/0241824 A1    Dec. 2, 2004

Related U.S. Application Data

(60) Provisional application No. 60/275,642, filed on Mar. 15, 2001.

(30) Foreign Application Priority Data

Mar. 15, 2001  (EP) ..................................... 01106544

(51) Int. Cl.
*C12Q 1/68* (2006.01)
(52) U.S. Cl. .............................................. 435/6; 435/7.1
(58) Field of Classification Search ............... 435/6, 7.1, 435/7.2, 7.32, 7.33, 7.92, 7.95, 91.2, 174, 435/243, 252.1, 259; 436/174, 177, 513, 436/536, 538
See application file for complete search history.

(56) References Cited

U.S. PATENT DOCUMENTS
5,702,895 A * 12/1997 Matsunaga et al. ................ 435/6

FOREIGN PATENT DOCUMENTS
| EP | 0 625 575 A | 11/1994 |
| WO | WO 92/05281 A | 4/1992 |
| WO | WO 99/16780 A | 4/1999 |

OTHER PUBLICATIONS

Niemeyer et al. 1997. Analytical Biochem. vol. 246: pp. 140-145.*
Sano et al. 1992. Science. vol. 258: pp. 120-122.*
Towner et al. J. 1998. Med. Microbiol. vol. 47: pp. 607-613.*
Francois et al. (J. Clin. Microbiol., 41:254-260, 2003).*
BLAST alignment for Y14051, Aug. 13, 2009.*
BLAST alignment for U23713, Aug. 13, 2009.*
BLAST alignment for X17688, Aug. 13, 2009.*
Nagahara et al., "A simple method for detection of *Staphylococcus aureus* using anti-protein A igY," *Journal of the Food Hygenic Society of Japan* (Oct. 1998), vol. 39, No. 5, pp. 318-323, Database Biosis 'Online!, Biosciences Information Service, Philadelphia, PA, US; Database accession No. PREV199900059917, XP002187201, ISSN: 0015-6426.
Wilkerson et al., "Comparison of five agglutination tests for identification of *Staphylococcus aureus*," *Journal of Clinical Microbiology* (1997), vol. 35, No. 1, pp. 148-151, XP001051889, ISSN: 0095-1137.
Ünal et al., "Detection of methycillin-resistant staphylococci by using the polymerase chain reaction," *Journal of Clinical Microbiology* (Jul. 1992), vol. 30, No. 7, pp. 1685-1691, XP002099980, ISSN: 00951137.

* cited by examiner

*Primary Examiner* — Gary B. Nickol
*Assistant Examiner* — Brian J Gangle
(74) *Attorney, Agent, or Firm* — Kratz, Quintos & Hanson, LLP

(57) ABSTRACT

Described is a method for the detection and quantification of methicillin-resistant *Staphylococcus aureus* from a specimen comprising a) contacting the specimen with Anti-Protein A antibodies so as to adsorb methicillinresistant *Staphylococcus aureus* and/or methicillin-sensitive *Staphylococcus aureus*, b) separating said antibodies to which methicillin-resistant *Staphylococcus aureus* and/or methicillin-sensitive *Staphylococcus aureus* have been adsorbed from the specimen, c) lysing methicillin-resistant *Staphylococcus aureus* and/or methicillin-sensitive *Staphylococcus aureus* adsorbed to said antibodies so as to release their DNA, d) combining the released DNA with (i) probes and/or primers which are specific for a target DNA sequence of the mecA gene of methicillin -resistant *Staphylococcus aureus* and/or of methicillin-resistant *Staphylococcus epidermis*, (ii) probes and/or primers which are specific for a target DNA sequence of methicillin-resistant *Staphylococcus aureus* other than a target DNA sequence of the mecA gene and (iii) probes and/or primers which are specific for a target DNA sequence of methicillin-resistant *Staphylococcus epidermis* other than a target DNA sequence of the mecA gene, whereby the target DNA sequences of methicillin-resistant *Staphylococcus aureus* and of methicillin-resistant *Staphylococcus* epidermis are not homologous, e) subjecting the combined released DNA and the specific probes and/or primers to conditions which permit amplification of said target DNA sequences, f) detecting the presence and amount of the amplified target DNA sequences as an indication of the presence and amount of methicillin-resistant *Staphylococcus aureus*, new primers and probes and diagnostic kits for the detection and quantification of MRSA.

26 Claims, No Drawings

SEQUENCE LISTING

<160> NUMBER OF SEQ ID NOS: 15

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Primer
      specific for a target DNA sequence of the mecA gene of MRSA and/or
      MRSE

<400> SEQUENCE: 1
cattgatcgc aacgttcaat tt                                            22

```
<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Primer
      specific for a target DNA sequence of the mecA gene of MRSA and/or
      MRSE

<400> SEQUENCE: 2
tggtctttct gcattcctgg a                                              21

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Probe
      specific for a target DNA sequence of the mecA gene of MRSA and/or
      MRSE

<400> SEQUENCE: 3
tgtggaagtt agattgggat catagcgtca t                                   31

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Primer
      specific for a target DNA sequence of the femA gene of MRSA

<400> SEQUENCE: 4
tgcctttaca gatagcatgc ca                                             22

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Primer
      specific for a target DNA sequence of the femA gene of MRSA

<400> SEQUENCE: 5
agtaagtaag caagctgcaa tgacc                                          25

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Probe
      specific for a target DNA sequence of the femA gene of MRSA

<400> SEQUENCE: 6
tcatttcacg caaactgttg gccactatg                                      29

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Primer
      specific for a target DNA sequence of the femA gene of MRSE

<400> SEQUENCE: 7
caactcgatg caaatcagca a                                              21
```

```
<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Primer
      specific for a target DNA sequence of the femA gene of MRSE

<400> SEQUENCE: 8
gaaccgcata gctccctgc                                                    19

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Probe
      specific for a target DNA sequence of the femA gene of MRSE

<400> SEQUENCE: 9
tactacgctg gtggaacttc aaatcgttat cg                                     32

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Primer
      specific for a target DNA sequence of the femA gene of MRSA

<400> SEQUENCE: 10
gctggtggta catcaaatgc a                                                 21

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Primer
      specific for a target DNA sequence of the femA gene of MRSA

<400> SEQUENCE: 11
cggtcaatgc catgatttaa tg                                                22

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Probe
      specific for a target DNA sequence of the femA gene of MRSA

<400> SEQUENCE: 12
tcattttgcc ggaagttatg cagtgca                                           27

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Primer
      specific for a target sequence of the femA gene of MRSE

<400> SEQUENCE: 13
cccatctctg ctggcttctt t                                                 21

<210> SEQ ID NO 14
```

```
-continued

<211> LENGTH: 18
<212> TYPE: DNA
<213> ORGANISM: Artificial sequence
<220> FEATURE:
<223> OTHER INFORMATION: Description of Artificial Sequence: Primer
      specific for a target DNA sequence of the femA gene of MRSE

<400> SEQUENCE: 14
ccgcatagct ccctgcaa                                                    18

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Probe
      specific for a target DNA sequence of the femA gene of MRSE

<400> SEQUENCE: 15
cgctggtgga acttcaaatc gttatcg                                          27
```

METHOD FOR THE DIRECT DETECTION OF METHICILLIN-RESISTANT *STAPHYLOCOCCUS AUREUS*

The present invention relates to a novel method for the detection and quantification of methicillin-resistant *Staphylococcus aureus* (MRSA) from a specimen. Furthermore, the present invention relates to new primers and probes and diagnostic kits for the detection and quantification of MRSA.

MRSA is a pathogenic bacterium and belongs to the class of multiresistant bacteria. The increasing prevalence of MRSA has become a major clinical problem. Therefore, rapid and accurate detection and identification of MRSA in clinical specimen are considered to be critical toward the prevention and treatment of infectious diseases.

Methods for the detection and identification of MRSA have already been described. For example, DNA-based methods employing PCR and amplification primers for the species-specific detection, identification and quantification of *Staphylococci* and of the antibiotic resistance gene coding for methicillin-resistance (mecA gene) has been described in WO 98/20157.

WO 99/16780 describes the use of primers specific for the mecA gene and *Staphylococcus* species-specific primers for the femA gene, a regulatory gene involved in cell wall metabolism, for amplification using multiplex PCR. Taking endotracheal aspirates as specimen, susceptible *Staphylococcus aureus* and methicillin resistant coagulase-negative *Staphylococci* were detected by electrophoresis.

U.S. Pat. No. 5,702,895 describes a multiplex PCR method for the detection of MRSA using biotin-labelled and dinitrophenyl-labelled primers for mecA and the spa gene, a marker which distinguishes *Staphylococcus aureus* from other *Staphylococci*. Specimens were taken from cultures of isolated bacteria and amplified DNA was detected by absorbance.

The methods described have been used only for the analysis of specimens taken from cultures of isolated bacteria and sterile sites. When a non-sterile specimen is used, however, the number of MRSA contained therein may be small and further *Staphylococci* such as methicillin-sensitive *Staphyloccoccus aureus* (MSSA) and methicillin-sensitive *Staphylococcus* epidermidis (MSSE) as well as methicillin-resistant *Staphylococcus* epidermidis (MRSE) may be present. Under such situations the methods described are disadvantageous in that the occurrence of the mecA gene cannot be linked explicitly and unequivocally to the presence of MRSA. Furthermore, under such conditions the risk of non-specific amplification cannot be excluded completely and sensitivity of the method is decreased.

The object of the present invention is to provide an improved method for the detection and quantification of MRSA from a specimen which allows for highly sensitive quantification of MRSA even if the specimen is from a non-sterile site.

This object has been achieved with a novel method according to claim 1.

According to the invention methicillin-resistant *Staphylococcus aureus* are detected and quantified from a specimen comprising a) contacting the specimen with Anti-Protein A antibodies so as to adsorb methicillin-resistant *Staphylococcus aureus* and/or methicillin-sensitive *Staphylococcus aureus*, b) separating said antibodies to which methicillin-resistant *Staphylococcus aureus* and/or methicillin-sensitive *Staphylococcus aureus* have been adsorbed from the specimen c) lysing methicillin-resistant *Staphylococcus aureus* and/or methicillin-sensitive *Staphylococcus aureus* adsorbed to said antibodies so as to release their DNA, d) combining the released DNA with (i) probes and/or primers which are specific for a target DNA sequence of the mecA gene of methicillin-resistant *Staphylococcus aureus* and/or of methicillin-resistant *Staphylococcus* epidermidis, (ii) probes and/or primers which are specific for a target DNA sequence of methicillin-resistant *Staphylococcus aureus* other than a target DNA sequence of the mecA gene and (iii) probes and/or primers which are specific for a target DNA sequence of methicillin-resistant *Staphylococcus* epidermidis other than a target DNA sequence of the mecA gene, whereby the target DNA sequences of methicillin-methicillin resistant *Staphylococcus aureus* and of methicillin-resistant *Staphylococcus* epidermidis are not homologous, e) subjecting the combined released DNA and the specific probes and/or primers to conditions which permit amplification of said target DNA sequences, f) detecting the presence and amount of the amplified target DNA sequences as an indication of the presence and amount of methicillin-resistant *Staphylococcus aureus*.

Specimen

Specimens from which MRSA can be detected and quantified with the present invention are from sterile and/or non-sterile sites. Sterile sites from which specimens can be taken are body fluids such as blood, urine, cerebrospinal fluid, synovial fluid, pleural fluid, pericardial fluid, intraocular fluid, tissue biopsies or endotracheal aspirates. Cultures of isolated bacteria are defined herein as well as sterile sites. Non-sterile sites from which specimens can be taken are e.g. sputum, stool, swabs from e.g. skin, inguinal, nasal and/or throat. Preferably, specimens from non-sterile sites, more preferably inguinal and/or nasal swabs are used in the present invention.

Contacting the Specimen with Anti-Protein A Antibodies

Usually, the specimen will be resuspended in e.g. saline, broth solution or bacterial culture medium such as CS medium (Brain-Heart Infusion with colistin and 2.5% NaCl) before being contacted with the Anti-Protein A antibodies. Usually, passivating agents e.g. serum albumin will be added to the resuspended specimen.

Anti-Protein A antibodies used in the present invention are antibodies directed to Protein A of MRSA and MSSA and are usually monoclonal antibodies. In order to allow for adsorption of MRSA and/or MSSA, the specimen will be usually contacted for 5 to 120 minutes, preferably for 10 to 60 minutes with the antibodies.

After adsorption of MRSA and/or MSSA has taken place, the antibodies will be separated from the specimen. Depending on the employed method of separation Anti-Protein A antibodies or modified e.g. biotinylated Anti-Protein A antibodies, both commercially available can be used in the present invention. The specimen and the antibodies can be separated by e.g. centrifugation, chromatography e.g. affinity chromatography or immobilisation of the antibodies or a combination of these methods. If immobilisation or affinity chromatography is used the antibodies can alternatively be immobilised or interact with the affinity column first and might then be contacted with the specimen.

Preferably, immobilisation of Anti-Protein A antibodies is used in the present invention to separate the antibodies having adsorbed MRSA and/or MSSA from the specimen. In particular a centrifugation step is added before immobilising the antibodies. The antibodies can be immobilised on e.g. paramagnetic beads. Streptavidin and biotin can be used as binding partners, e.g. by linking biotinylated Anti-Protein A antibodies to streptavidin coated paramagnetic beads. Preferably, biotinylated Anti-Protein A antibodies and streptavidin coated paramagnetic beads are used to immobilise the antibodies. Streptavidin coated paramagnetic beads are commercially available. Usually, the antibodies and the paramagnetic beads will be incubated to allow for binding of the antibodies to the paramagnetic beads and then will be held magnetically to separate from the specimen by washing the paramagnetic beads. The incubation period is usually 5 to 120 minutes, preferably 10 to 60 minutes. The period to held the paramagnetic beads magnetically is usually 1 to 60 minutes, preferably 2 to 20 minutes.

The antibodies can be resuspended during separation if necessary. For resuspending and washing e.g. phosphate buffered saline containing human serum albumin can be used.

Lysing of the Microorganisms Adsorbed to Release their DNA

MRSA and/or MSSA adsorbed to the antibodies can be lysed to release their DNA by e.g. applying a detergent such as TWEEN (®, polysorbate nonionic detergent), TRITON X-100 (®, nonionic detergent), an alkali such as NaOH, a protease such as proteinase K or a chaotroph and/or shear forces. The lysis is usually carried out in a buffer like TE (Tris-HCl 10 mM, pH=8 and EDTA 1 mM) or in water (molecular grade purity) or in a buffer like phosphate-buffered saline (PBS) or in saline.

As chaotroph e.g. guanidinium isothiocyanate, urea or guanidine hydrochloride, preferably guanidinium isothiocyanate is used. In case a chaotroph is used ATL buffer (®,edetic acid/sodium dodecyl sulfate buffer) commercialized by Qiagen which contains guanidinium isothiocyanate is preferably used. In case a chaotroph is used, it is removed from the released DNA after lysis by e.g contacting the released DNA to a DNA binding column such as Q1AMP (®, Qiagen). The DNA eluted from the column can be then combined with the probes and/or the primers or can be concentrated before.

Shear forces can be applied by e.g. adding beads and mixing the solution. As beads, preferably glass beads, more preferably glass beads with a diameter of 100-200 μm as commercialised by Schieritz and Hauenstein AG (Switzerland) can be added. The use of glass beads is particularly useful since it has been found that if the lysis is carried out in PBS or in saline glass beads, particularly glass beads with a diameter of 100-200 μm as commercialised by Schieritz and Hauenstein AG (Switzerland) quantitatively bind the released DNA which efficiently extracts DNA from other components. After elution of the DNA bound to the glass beads using water or TE, the eluted DNA can be combined directly with the probes and/or the primers or can be concentrated before. Alternatively glass beads with bound DNA can be suspended in PBS or in saline and can be directly combined with the probes and/or the primers.

In addition lysis applying shear forces can be carried out as well in TE (Tris-HCl 10 mM, pH=8 and EDTA 1 mM) or in water (molecular grade purity) using beads, preferably glass beads, more preferably glass beads with a diameter of 100-200 μm as commercialised by Schieritz and Hauenstein AG (Switzerland). This procedure allows for direct recovery of the DNA in the liquid phase. The DNA in the liquid phase can be combined directly with the probes and/or the primers or can be concentrated before.

The preferred way to carry out the lysis is to use shear forces. More preferably the lysis is carried out in a buffer like (PBS) or in saline, using glass beads, particularly glass beads with a diameter of 100-200 μm as commercialised by Schieritz and Hauenstein AG (Switzerland).

Probes and/or Primers

The probes and/or primers of the present invention which are specific for a target DNA sequence of the mecA gene of MRSA and/or MRSE, a target DNA sequence of MRSA other than a target DNA sequence of the mecA gene and a target DNA sequence of MRSE other than a target DNA sequence of the mecA gene encompass the particular sequence of the particular probe and/or primer, a sequence complementary therof, a part therof having at least 10, preferably 15, more preferably 20 nucleotides in length and a variant thereof. Variants encompass degenerated sequences, deletions, insertions and substitutions at one or more nucleotide position, as long as each particular primer or probe is still specific for the particular target DNA sequence. Usually, probes and primers are applied for each target DNA sequence. Preferably, a pair of primers such as a forward primer and a reverse primer, and a probe are applied.

The terms "specific probes and/or primers" or "probes and/or primers which are specific for a target DNA sequence" as used herein refer to probes, which have a homology of higher than 60%, preferably higher than 70%, more preferably higher than 80%, in particular higher than 90% with the particular target DNA sequence to be amplified and primers which have a homology of higher than 60%, preferably higher than 70%, more preferably higher than 80%, in particular higher than 90% with the DNA flanking the particular target DNA sequence to be amplified. The probes and primers, respectively, hybridize under stringent conditions e.g. at a temperature of between 55 and 65° C., preferably between 58 and 62° C. and at a given salt concentration of between 3 and 10 mM, preferably between 4 and 6 mM, with the complement of the particular target DNA sequence to be amplified and with the DNA flanking the complement of the particular target DNA sequence to be amplified, respectively.

As a basis to select (i) probes and/or primers which are specific for a target DNA sequence of the mecA gene of MRSA and/or MRSE, (ii) probes and/or primers which are specific for a target DNA sequence of MRSA other than a target DNA sequence of the mecA gene and (iii) probes and/or primers which are specific for a target DNA sequence of MRSE other than a target DNA sequence of the mecA gene, database sequences such as GenBank or EMBL, fragments described in the literature or isolated fragments of the respective microorganism can be used. Preferably, database sequences such as GenBank or EMBL, more preferably GenBank is used. In particular, probes and/or primers which are specific for a target DNA sequence of the mecA gene of MRSA and/or MRSE are selected from the mecA gene sequence comprised by sequence number Y14051 (Genbank), (ii) probes and/or primers which are specific for a target DNA sequence of MRSA other than a target DNA sequence of the mecA gene are selected from the femA gene sequence of MRSA comprised by sequence number X17688 (Genbank) and (iii) probes and/or primers which are specific for a target DNA sequence of MRSE other than a target DNA sequence of the mecA gene gene are selected from the femA gene sequence of MRSE comprised by sequence number U23713 (Genbank).

Probes and/or primers which are specific for a target DNA sequence of MRSA other than a target DNA sequence of the mecA gene can be as well selected from database sequences such as GenBank or EMBL, fragments described in the literature or isolated fragments of the respective microorganism which comprise target DNA sequences of MSSA provided that these target DNA sequences are as well harboured by MRSA.

Probes and/or primers which are specific for a target DNA sequence of MRSE other than a target DNA sequence of the mecA gene can be as well selected from database sequences such as GenBank or EMBL, fragments described in the literature or isolated fragments of the respective microorganism which comprise target DNA sequences of MSSE provided that these target DNA sequences are as well harboured by MRSE.

Usually, it will be sufficient to select one target DNA sequence of the mecA gene of MRSA or MRSE to design the probes and the primer which are specific for a target DNA sequence of the mecA gene of MRSA and/or MRSE since the mecA gene is between 95% and 100% usually higher than 97% homologous between MRSA and MRSE. Preferably, the selected target DNA sequence of the mecA gene is from MRSA.

As target DNA sequences gene of MRSA and MRSE which are not homologous every DNA sequence other than a target DNA sequence of the mecA gene which is harboured by 100% of MRSA and 100% of MRSE, respectively, can be used provided that the homology between both target DNA sequences is lower than 90%, preferably lower than 85%, most preferably lower than 80% and that both sequences do not crosshybridize under the stringent conditions described above. Usually target DNA sequences of a gene such as the femA gene of MRSA (femA-SA) and the femA gene of MRSE (femA-SE) or other target DNA sequences of genes of MRSA and MRSE which are not related to each other are used as target DNA sequences. Preferably, target DNA sequences of the femA gene of MRSA (femA-SA) and of the femA gene of MRSE (femA-SE) are used.

The probes and/or primers which are specific for a target DNA sequence of the mecA gene of MRSA and/or MRSE, a target DNA sequence of MRSA other than a target DNA sequence of the mecA gene and a target DNA sequence of MRSE other than a target DNA sequence of the mecA gene are usually designed to generate an amplification product of approximately 100+/−50 nucleotides. The sequence of the primers and probes can be obtained by using standard programs and primer analysis software such as "Primer Express" (®, Perkin Elmer) and can be synthesised using standard methods such as an automated DNA synthesizer Primers which are specific for a target DNA sequence of the mecA gene of MRSA and/or MRSE usually consist of 13-30, preferably 20-26 nucleotides in length. Probes which are specific for a target DNA sequence of the mecA gene of MRSA and/or MRSE usually consist of 15-40, preferably 25-35, nucleotides in length.

Primers which are specific for a target DNA sequence of MRSA other than a target DNA sequence of the mecA gene and for a target DNA sequence of MRSE other than a target DNA sequence of the mecA gene usually consist of 13-30, preferably 20-26 nucleotides in length and are usually selected in order to contain >3 mismatches to discriminate target DNA sequence of MRSA other than a target DNA sequence of the mecA gene from the target DNA sequence of MRSE other than a target DNA sequence of the mecA gene. Probes which are specific for a target DNA sequence of MRSA other than a target DNA sequence of the mecA gene and for a target DNA sequence of MRSE other than a target DNA sequence of the mecA gene usually consist of 15-40, preferably 25-35, nucleotides in length and are usually selected in order to contain >3 mismatches to discriminate target DNA sequence of MRSA other than a target DNA sequence of the mecA gene from the target DNA sequence of MRSE other than a target DNA sequence of the mecA gene.

All primers and probes can be selected to be compatible with each other as well as with the other sets of primers and probes in order to avoid self-hybridisation or hybridisation between different primers and/or probes, loop-formation and false priming site. After selection the primers and probes can be tested in pairs to assess their sensitivity and specificity and can be combined in different concentrations of usually 50-900 nM, to define optimal reaction conditions during amplification.

Preferred probes and/or primers specific for a target DNA sequence of the mecA gene of MRSA and/or MRSE are selected from the primers comprising the sequences SEQ ID No. 1 and 2 and the probe comprising the sequence SEQ ID No. 3, a sequence complementary therof, a part therof having at least 10, preferably 15, more preferably 20 nucleotides in length and a variant thereof. Particular preferred probes and/or primers specific for a target DNA sequence of the mecA gene of MRSA and/or MRSE are the primers comprising the sequences SEQ ID No. 1 and 2 and the probe comprising the sequence SEQ ID No. 3.

Preferred probes and/or primers specific for a target DNA sequence of MRSA other than a target DNA sequence of the mecA gene are probes and/or primers, a sequence complementary therof, a part therof having at least 10, preferably 15, more preferably 20 nucleotides in length and a variant thereof which are specific for a target DNA sequence of the femA gene of MRSA.

Particular preferred probes and/or primers specific for a target DNA sequence of the femA gene of MRSA are selected from the primers comprising the sequences SEQ ID No. 4 and 5 and the probe comprising the sequence SEQ ID No. 6, and the primers comprising the sequences SEQ ID No. 10 and 11 and the probe comprising the sequence SEQ ID No. 12, a sequence complementary therof, a part therof having at least 10, preferably 15, more preferably 20 nucleotides in length and a variant thereof. Most preferred are the primers comprising the sequences SEQ ID No. 4 and 5 and the probe comprising the sequence SEQ ID No. 6 and the primers comprising the sequences SEQ ID No. 10 and 11 and the probe comprising the sequence SEQ ID No. 12, in particular the primers comprising the sequences SEQ ID No. 10 and 11 and the probe comprising the sequence SEQ ID No. 12.

Preferred probes and/or primers specific for a target DNA sequence of MRSE other than a target DNA sequence of the mecA gene are probes and/or primers, a sequence complementary therof, a part therof having at least 10, preferably 15, more preferably 20 nucleotides in length and a variant thereof which are specific for a target DNA sequence of the femA gene of MRSE.

Particular preferred probes and/or primers specific for a target DNA sequence of the femA gene of MRSE are selected from the primers comprising the sequences SEQ ID No. 7 and 8 and the probe comprising the sequence SEQ ID No. 9 and the primers comprising the sequences SEQ ID No. 13 and 14 and the probe comprising the sequence SEQ ID No. 15, a sequence complementary therof, a part therof having at least 10, preferably 15, more preferably 20 nucleotides in length and a variant thereof. Most preferred are the primers comprising the sequences SEQ ID No. 7 and 8 and the probe comprising the sequence SEQ ID No. 9 and the primers comprising the sequences SEQ ID No. 13 and 14 and the probe comprising the sequence SEQ ID No. 15, in particular the primers comprising the sequences SEQ ID No. 13 and 14 and the probe comprising the sequence SEQ ID No. 15.

Amplification

Conditions which permit amplification of said target DNA sequences are well known to the person skilled in the art.

Usually, an amplification method such as polymerase chain reaction (PCR), nested PCR or multiplex PCR, ligase chain reaction, nucleic acid sequence-based amplification (NASBA), self-sustained sequence replication (3SR), strand displacement amplification (SDA), branched DNA signal amplification (bDNA), transcription-mediated amplification (TMA) or cycling probe technology (CPT) can be used. Preferably, multiplex PCR is used. In a multiplex PCR the aforementioned probes and/or primers are used in combination in a single PCR reaction together with the released DNA.

In case a PCR method is used as amplification method e.g. a DNA polymerase as Taq DNA polymerase (Perkin Elmer) or AmpliTaq® (DNA polymerase, PE Applied Biosystems), Hot GoldStar Taq polymerase (Eurogentec), AmpliTaq Gold® polymerase (DNA polymerase, PE Applied Biosystems), SureStart™ Taq (DNA polymerase, Stratagene) or Platinum Taq® (DNA polymerase, Gibco) can be used. Preferably, Hot GoldStar Taq DNA polymerase is used. The treatment to denature into a single-stranded DNA is usually a thermal treatment. Usual PCR conditions are e.g. thermal cycling conditions like incubation for 0.5-5 at 40°-60°, preferably 1.5-2.5 min. at 45°-55°, followed by incubation for 5-15 min. at 90°-97°, preferably 8-12 min. at 95°, followed by incubation for 5-30 sec. at 90°-97°, preferably 10-20 at 95°, followed by incubation for 0.1-5 min. at 50°-70°, preferably 0.5-2 min. at 55°-65°, the last two incubation steps will be repeated up to 100 times preferably 50 times. A further denaturation step can be added as first incubation step in case a DNA polymerase is used.

Usually a commercially available reaction buffer is added to the released DNA combined with the probes and/or primers before incubation. The probes and/or primers are usually added in excess to the released DNA. Usual ratios of probe and primers for each target DNA sequence are between 1/3 and 2/1. The ratio of one primer over the other for each target DNA sequence are usually between 1/3 and 3/1.

The presence and amount of the amplified target DNA sequences can be detected by e.g. a method in which the size of the amplified target DNA sequences is confirmed by electrophoresis, by hybridizing the amplified target DNA sequences with a labelled probe having sequence complementary to the sequence of the target amplified or by real-time PCR, wherein amplified target DNA sequences are detected during amplification e.g. by measuring during amplification using a variety of fluorescent dyes emitting at different wavelengths. Real-time PCR systems such as TaqMan® (Perkin Elmer), ABI Prism Sequence Detection Systems (Applied Biosystems), SmartCycler® (Cepheid), I-Cycler (BioRad), LightCycler® (Roche), R.A.P.I.D. (Idaho Technologies), DNA Engine Opticon® (MJ Research), RotorGene (Corbett Research), and MX400 (Stratagene) are the preferred methods. Particulary preferred are the ABI Prism Sequence Detection Systems, the TaqMan® and the SmartCycler® system. Most preferred are the ABI Prism Sequence Detection Systems. Different fluorescent dyes and non-non fluorescent quenchers depending on real-time PCR the system used can be coupled with e.g. each of the said probes prior to amplification e.g. a fluorescent dye such as FAM (6-carboxyfluorescein), HEX (6-carboxy-2',4,4',5',7,7'-hexachlorofluorescein), TET (6-carboxy -4,7,2',7'-tetrachloro-fluorescein), JOE (6-carboxy-4',5'-dichloro-2',7'-dimethoxy fluorescein) or Texas-Red® can be coupled at the 5'-end of the probe and a fluorescent quencher such as TAMRA (6-carboxy-N,N,N', N'-tetramethylrhodamine) or a non-fluorescent quencher such as DABCYL (4-((4-(dimethylamino)phenyl)azo)benzoic acid) can be coupled at the 3'-end of the probe. In case real-time PCR is used, usually the cycle threshold (Ct) of the amplified target DNA sequences is detected whereby the difference of the Cts obtained for the target DNA sequence of the mecA gene of MRSA and/or MRSE and obtained for the target DNA sequence MRSE other than the mecA gene indicates the presence and amount of MRSA.

The preferred conditions which indicate the presence and amount of MRSA are when all following requirements are met:
1) Smallest Ct for target DNA sequence of the mecA gene of MRSA and/or MRSE<40
2) Smallest Ct for target DNA sequence of MRSA other than the mecA gene<40
3) Difference between Ct for target DNA sequence of the mecA gene of MRSA and/or MRSE and Ct for target DNA sequence of MRSE other than the mecA gene (Ct target DNA sequence of the mecA gene of MRSA and/or MRSE−Ct target DNA sequence of MRSE other than the mecA gene)≦0

Preferably the difference between Ct for target DNA sequence of the mecA gene of MRSA and/or MRSE and the Ct for target DNA sequence of MRSE other than the mecA gene is <0, more preferably between <0 and −1, in particular between −0.25 and −0.75.

MRSA is absent in all other conditions.

Usually, DNA from control strains are combined with the specific probes and/or primers and are amplified under the same conditions as the DNA target sequences described supra in order to determine Ct for each DNA target sequence. As control strains e.g. MRSA, MRSE, MSSE, MSSA strains, particularly ATCC33591 (MRSA), ATCC25923 (MSSA), Clinical isolates from nasal swabs (MRSE) and ATCC12228 (MSSE) can be used.

The term cycle threshold (Ct) used herein refers to the particular cycle of amplification which allows for unequivocal detection of the amplified product calculated as 6-12 times, preferably 8 times, the standard deviation of the background.

The Ct for the DNA target sequences is usually set by determining the background for each fluorescent dye as the average fluorescence value measured during 3-18 cycles, preferably 3-12 cycles. After background subtraction, the cycle threshold for the target DNA sequence of MRSA other than a target DNA sequence of the mecA gene can be calculated as 6-12 times, preferably 8 times, the standard deviation of the background. A similar calculation can be performed for the target DNA sequence of MRSE other than a target DNA sequence of the mecA gene. The threshold value for the target DNA sequence of MRSE other than a target DNA sequence of the mecA gene can be compared with the Ct obtained from a MRSE control strain. The threshold value for the DNA target sequences of the mecA gene can be then adjusted so that the Ct for the DNA target sequences of the mecA gene is equal to the Ct for the target DNA sequence of MRSA other than a target DNA sequence of the mecA gene. This adjustment is usually performed by comparing with Ct for the target DNA sequence of the mecA gene and the target DNA sequence of MRSA other than a target DNA sequence of the mecA gene obtained from a MRSA control strain. Usually, 100 pg total DNA of the control strain is used per amplification run to determine Ct for the target DNA sequence of the mecA gene, for the target DNA sequence of MRSA and for the target DNA sequence of MRSE. Preferably an internal control is used by adding usually 1-100 pg, preferably 1 pg, of a target DNA sequence other than a target DNA sequence of the mecA gene, preferably a target DNA sequence of the femA gene of MSSA, from an MSSA strain such as strain ATCC25923 (MSSA) to the reaction buffer before carrying out the amplification method. In case an internal control is used the presence and amount of MRSA is usually indicated when:

1) Smallest Ct for target DNA sequence of the mecA gene of MRSA and/or MRSE<40
2) Smallest Ct for target DNA sequence of MRSA other than the mecA gene<40
3) Difference between Ct for target DNA sequence of the mecA gene of MRSA and/or MRSE and Ct for target DNA sequence of MRSE other than the mecA gene (Ct target DNA sequence of the mecA gene of MRSA and/or MRSE−Ct target DNA sequence of MRSE other than the mecA gene) <0

MRSA is absent in all other conditions. In case an internal control is used, the presence and amount of MRSA is preferably indicated when the difference between Ct for target DNA sequence of the mecA gene of MRSA and/or MPSE and Ct for target DNA sequence of MRSE other than the mecA gene (Ct target DNA sequence of the mecA gene of MRSA and/or MRSE−Ct target DNA sequence of MRSE other than the mecA gene) is between <0 and −1, more preferably between −0.25 and −0.75. Consequently the addition of an internal control allows to determine only two Cts, Ct for target DNA sequence of the mecA gene of MRSA and/or MRSE and Ct for target DNA sequence of MRSE other than the mecA gene, in order to indicate the presence and amount of MRSA. Ct for target DNA sequence of MRSA other than the mecA gene can be additionally determined and should be <40 for considering the run as valid.

Further objects of the present invention are primers and/or probes specific for a target DNA sequence of the mecA gene of MRSA and/or MRSE selected from the primers comprising the sequences SEQ ID No. 1 and 2 and the probe comprising the sequence SEQ ID No. 3, a sequence complementary therof, a part therof having at least 10, preferably 15, more preferably 20 nucleotides in length and a variant thereof; primers and/or probes specific for a target DNA sequence of the femA gene of MRSA selected from the primers comprising the sequences SEQ ID No. 4 and 5 and the probe comprising the sequence SEQ ID No. 6, and the primers comprising the sequences SEQ ID No. 10 and 11 and the probe comprising the sequence SEQ ID No. 12, a sequence complementary therof, a part therof having at least 10, preferably 15, more preferably 20 nucleotides in length and a variant thereof; and primers and/or probes specific for a target DNA sequence of the femA gene of MRSE selected from the primers comprising the sequences SEQ ID No. 7 and 8 and the probe comprising the sequence SEQ ID No. 9 and the primers comprising the sequences SEQ ID No. 13 and 14 and the probe comprising the sequence SEQ ID No. 15, a sequence complementary therof, a part therof having at least 10, preferably 15, more preferably 20 nucleotides in length and a variant thereof.

A further object of the present invention is a diagnostic kit for the detection of methicillin-resistant *Staphylococcus aureus* in a specimen comprising any suitable combination of the nucleic acids having the nucleotide sequences of any one of SEQ ID No. 1, 2, 3, 4, 5, 6, 7, 8, 9, 10, 11, 12, 13, 14 and 15 a sequence complementary therof; a part therofhaving at least 10, preferably 15, more preferably 20 nucleotides in length and a variant thereof comprising in addition the aforementioned Anti-Protein A antibodies. Preferably, the kit comprises in addition to the aforementioned Anti-Protein A antibodies glass beads.

EXAMPLES

Example 1

Selection and Synthesis of Primers and Probes

Target DNA sequences of the mecA gene of MRSA, of the femA gene of MRSA and of the femA gene of MRSE were selected from Genbank sequence database.

The Genbank sequences of the femA gene of MRSE (femA-SE, from Genbank sequence U23713) and of the femA gene of MRSA (femA-SA, from Genbank sequence X17688) have been aligned using the "Clustal" alignment method (Baylor College of Medicine) and the regions showing the poorest level of homology were detected. The research of primers and probes, restricted to those partial sequences has been done using "Primer Express" (®, Perkin Elmer software developed for Taqman®, applications). Probes and primers were designed in the aim to generate short PCR fragments (approximately 100+/−50 nucleotides). Probes and primers specific for target DNA sequences of femA-SA and of femA-SE were designed to consist of nucleotides containing at least >3 mismatches to discriminate between the sequence of femA-SA and femA-SE.

Pure DNA preparations of the control strains ATCC25923 (MSSA) and ATCC12228 (MSSE) allowed to test the specificity of the selected primers/probes. No cross reaction was recorded in the Taqman® amplification assay, using the described probes and/or primers. The sequences SEQ ID No. 4, 5 and 6 amplified the region of nucleotide 651 to 788 of femA-SA. The sequences SEQ ID No. 7, 8 and 9 amplified the region of nucleotide 1403 to 1547 of femA-SE. The sequences SEQ ID No. 10, 11 and 12 amplified the region of nucleotide 1600 to 1694 of femA-SA. The sequences SEQ ID No. 13, 14 and 15 amplified the region of nucleotide 1315 to 1414 of femA-SE.

The amplified region of the mecA gene was 321 to 419 (mecA, from Genbank sequence Y14051). Based on the known sequences of the mecA gene, this region is highly conserved for *Staphylococcus aureus* (Y14051) and *Staphylococcus* epidermidis (Genbank sequence X52592).

All nucleotides have been synthesized and fluorescently labelled by Eurogentec (Seraing, Belgium) using Expedite™ automated synthesizer. The purification technique was based on an internally developed (Eurogentec) chromatography system, leading to equivalent or better performance than obtained using HPLC. All nucleotides (OliGold™) were delivered lyophilised, were deprotected and purified by reverse phase chromatography. The absence of salts, ammonium and acid residues was also checked. All reagents used for oligonucleotide synthesis were quality controlled as described in the Glen Research catalogue. The dyes used FAM, TET, HEX JOE or Texas Red® ((bound to the 5' end of the probe) and the quencher TAMRA or DABCYL (bound to the 3' end) are coupled using the appropriate phosphoramidite or succinimidyl ester derivatives (FAM: 6-carboxyfluorescein, TAMRA: 6-carboxy-N,N,N',N'-tetramethylrhodamine, HEX: 6-carboxy-2',4,4',5',7,7'-hexachloro-fluorescein, TET: 6-carboxy-4,7,2',7'-tetrachloro-fluorescein, JOE: 6-carboxy-4',5'-dichloro-2',7'-dimethoxy fluorescein, DABCYL: (4-((4-(dimethylamino)phenyl)azo)ben-zoic acid, or Texas Red®).

Primers and probes were tested to be mutually compatible with each other as well as with the other sets of primers and probes (multiplexing) in order to avoid self-hybridisation or hybridisation between different primers and/or probes, loop-formation and false priming site. Primers and probes were then tested in pairs to assess their sensitivity and specificity.

They were then combined in different concentrations (50-900 nM) to define optimal reaction conditions.

Example 2

Preconditioning of the Samples

Samples consisting in nasal/inguinal swabs were collected and possibly pooled for each patient by suspending them into CS medium (Brain-Heart Infusion with colistin and 2.5% NaCl). A preliminary study showed that this bacterial medium enriched in salt, bactericidal and nutritive agents did not influence the following steps and performed equally well as saline (0.9% NaCl). These samples (1 ml) were then supplemented by 50 µl of 20% human serum albumin (injectable grade from the Swiss Red Cross). The preconditioning of the samples required about 5 min.

Enrichment of the Sample 1.5 µl of a mouse biotinylated monoclonal antibody raised against *staphylococcal* protein A (Sigma) was then added to all samples, followed by 45-minutes incubation on a rotary shaker at room temperature conditions. Samples were then centrifuged for 10 minutes at 5000 g. The supernatant was removed before adding 200 µl of phosphate buffered saline containing 1% human serum albumin (PBS-HSA). Samples were mixed with 10 µl streptavidin-coated magnetic beads (ø=1 µm, Merck) and incubated on the rotary shaker for 45 minutes, in ambient conditions. Samples were then transferred into a 96 well plate and kept on a magnetic holder for 5 minutes (Milian). The supernatant was removed and the paramagnetic beads were rinsed twice in PBS-HSA. The enrichment of the sample required about 95 min.

Bacterial Lysis and Release of DNA

The paramagnetic beads were then suspended in the 96 well plate in 400 µl of chaotropic buffer (ATL buffer (®), edetic acid/sodium dodecyl sulfate buffer, from the kit Q1AMP,(®, Qiagen) and transferred into clean eppendorf tubes. Hundred milligrams of glass beads (ø=100-200 µm, Schieritz and Hauenstein AG, CH-4144 Arlesheim) were added and bacteria were lysed using a mixing apparatus (Mixer Mill, Qiagen) with 2 homogenisation cycles of 45 seconds each. After 10 minutes centrifugation at 5000 g, the liquid phase was placed into clean tubes and mixed with 200 µl of room-temperature pure ethanol. DNA was immobilized Q1AMP®, columns (Qiagen), rinsed as described by the manufacturer and eluted into a volume of 100 µl of pure water. The extracts were then dried in an evaporator (UniVapo 100H, UniEquip) for 1 hour and resuspended in 20 µl of pure water. The bacterial lysis and release of DNA required about 30 min.

Nucleic Acid Detection by Real-time PCR and Analysis

For the robustness of the analysis, each sample containing the released DNA was analysed in triplicate. Detection and analysis required about 150 min.

TaqMan™ system (Perkin Elmer) together with the Hot GoldStar Taq DNA polymerase (Eurogentec) were used for amplification of the samples.

A. Amplified Targets

TABLE 1

| | A<br>Forward<br>primer | B<br>Reverse<br>primer | C<br>Probe |
|---|---|---|---|
| 1 mecA | CATTGATCGCAAC GTTCAATTT | TGGTCTTTCTGCA TTCCTGGA | TGTGGAAGTTAGA TTGGGATCATAGC GTCAT |
| 2 femA-SA | TGCCTTTACAGAT AGCATGCCA | AGTAAGTAAGCAA GCTGCAATGACC | TCATTTCACGCAA ACTGTTGGCCACT ATG |
| 3 femA-SE | CAACTCGATGCAA ATCAGCAA | GAACCGCATAGCT CCCTGC | TACTACGCTGGTG GAACTTCAAATCG TTATCG |

Forward primer A1 corresponds to SEQ ID No. 1. Reverse primer B1 corresponds to SEQ ID No. 2. Probe C1 corresponds to SEQ ID No. 3. Forward primer A2 corresponds to SEQ ID No. 4. Reverse primer B2 corresponds to SEQ ID No. 5. Probe C2 corresponds to SEQ ID No. 6. Forward primer A3 corresponds to SEQ ID No. 7. Reverse primer B3 corresponds to SEQ ID No. 8. Probe C3 corresponds to SEQ ID No. 9.

The final volume of the PCR mixture was 25 µl and contained the following compounds:

Reaction buffer 2×: 12.5 µl (commercialized by Eurogentec)
A1: 75 nM, B1: 75 nM and C1: 100 nM
A2: 100 nM, B2: 100 nM and C2: 100 nM
A3: 100 nM, B3: 100 nM and C3: 100 nM
6 µl of the sample and the amplification run was immediately performed.

Fluorescent dyes linked to the probes were the following:
C1 (mecA) 5'-HEX and 3'-TAMRA
C2 (femA-SA) 5'-FAM and 3'-TAMRA
C3 (femA-SE) 5'-TET and 3'-TAMRA B. Amplification Conditions:

The assay has been developed according to Applied Biosystems specifications, except that 50 cycles were used to increase the sensitivity (without loss of specificity).

| incubation 1 → | 2 min. at 50° C. |
|---|---|
| incubation 2 → | 10 min. at 95° C. |
| incubation 3 → | 15 sec. at 95° C. |
| incubation 4 → | 1 min. at 60° C. |

(3 and 4 were repeated 50 times)

C. Analysis

After visual inspection of the data obtained, the background for each fluorescent reporter was determined as the average fluorescence value measured during cycles 3-12. After background subtraction, the threshold value for femA-SA was calculated as 6-12 times (preferably 8 times) the standard deviation of the background. A similar calculation was performed for femA-SE. Ct for femA-SE was determined using 100 pg DNA/well from control MRSE strain (isolate from a nasal swab) under the same conditions as described in A and B. The threshold value for mecA was then adjusted so that Ct for mecA=Ct for femA-SA. This determination was performed using 100 pg DNA/well from control MRSA strain (ATCC33591) under the same conditions as described in A and B. From screenshots obtained for femA-SA, mecA and femA-SE the smallest Ct among triplicates for each DNA target sequence was determined. MRSA was present when all following conditions were met:

1) Smallest Ct for mecA<40
2) Smallest Ct for femA-SA<40
3) Ct for mecA−Ct for femA-SE≦0
MRSA was absent in all other conditions.

Example 3

Alternative Method for Bacterial Lysis and Release of DNA
Bacterial lysis and release of DNA of Example 1 was alternatively carried out as follows:
a) Bacterial lysis was performed using glass beads in 0.9% sodium chloride (NaCl) solution. After lysis, the supernatant was discarded and the beads suspended in 200 to 400 µl of pure water. After vigorous agitation, eluted DNA (now in the liquid phase) was concentrated by evaporation, solubilized in 20 µl of water and used directly in the Taqman® amplification assay.
b) After bacterial lysis in the presence of 0.9% NaCl, the beads were rinsed twice with the same solution, then suspended with 100 µl of the saline solution. 6 µl aliquots of the beads suspension were directly introduced in the Taqman® amplification assay.
c) Bacterial lysis was performed suspending glass beads in 200 to 400 µl of pure water. After vigorous agitation, eluted DNA (now in the liquid phase) were concentrated by evaporation, solubilized in 20 µl of water and used directly in the Taqman® amplification assay.

Example 4

Evaluation of Sensitivity
Experiments using samples spiked with known amounts of MRSA and MRSE revealed a specificity of hundred percent and a sensitivity of 1 genome copy. A large range of spiked amounts has been tested from 10 ng to 0.1-0.2 fg/reaction (1 genome copy equivalent to $1.65 \times 10^{-15}$ g).

Example 5

Comparing Molecular Detection to Standard Culture-based Procedures
A middle scale study (38 samples treated simultaneously) comparing molecular detection to standard culture-based procedures performed by the Laboratoire Central de Microbiologie, LCB, Geneva University Hospital) allowed the detection of all positive culture cases (11/11). Two samples negative by culture were found positive using the molecular technique of example 1. For these 2 patients, the LCB found the presence of MRSA in another sampling site.

Example 6

A. Paramagnetic Enrichment of Mixed-samples Containing MRSA and MRSE
The samples were spiked with different ratios of MRSA and MRSE (from 1/1 to 1/1000). Samples were then either directly lysed (protocol a) or enriched by the method described in example 1 using anti protein A antibodies and paramagnetic beads (protocol b) and subject to amplification as described in example 2.
The results obtained showed that for the 1/1 ratio and despite the additional steps in protocol b, the Cts were increased by 1-2 cycles without enrichment (protocol a). This implies an increased sensitivity of protocol b over protocol a. For the 1/5 ratio the Ct for femA-SA were increased from 2-2.5 cycles without enrichment (protocol a). The increased sensitivity was more string when the ratio MRSA/MRSE decreased. For ratios lower than 1/5, no femA-SA signal was recorded using protocol a in the tested range of spiked bacteria. Using protocol b, no significant signal for femA-SE was recorded even with ratios lower than 1/5, indicating an excellent enrichment even in the presence of a large excess of MRSE.

B. Detection of MRSA and MRSE in the Presence of *Pseudomonas aeruginosa*
This experiment was based on a commonly encountered situation in clinical diagnosis where patients become colonized by *Pseudomonas aeruginosa*. Whenever *Pseudomonas aeruginosa* was spiked to the ratios as indicated in A, no femA SA signal could be recorded unless using the protocol b.
For all conditions using protocol b, the Ct of femA SA and Ct mecA were almost identical and the interpretation was straightforward, underlying the absolute need of this step for accurate and sensitive detection.

Example 7

Preconditioning and enrichment of the sample were carried out as described in example 2, except that the sample was suspended in PBS and then supplemented by 50 µl of 20% human serum albumin (injectable grade from the Swiss Red Cross). Bacterial lysis and release of DNA was carried out as described in example 3a) except that the enriched sample was resuspended in 50 µl of pure water before adding the glass beads. After shearing force disruption, the DNA contained in the liquid phase (10 µl) was directly added to the amplification mixture and subject to the Taqman® amplification assay.

Nucleic Acid Detection by Real-time PCR and Analysis
For the robustness of the analysis, each sample containing the released DNA was analysed in triplicate. Detection and analysis required about 150 min. ABI Prism Sequence Detection System cycler (Applied Biosystems) together with the Hot GoldStar Taq DNA polymerase (Eurogentec) was used for amplification of the samples.

A. Amplified Targets

TABLE 2

|   | A Forward primer | B Reverse primer | C Probe |
|---|---|---|---|
| 1 mecA | CATTGATCGCAAC GTTCAATTT | TGGTCTTTCTGCA TTCCTGGA | TGTGGAAGTTAGA TTGGGATCATAGC GTCAT |
| 4 femA-SA | GCTGGTGGTACAT CAAATGCA | CGGTCAATGCCAT GATTTAATG | TCATTTTGCCGGA AGTTATGCAGT GCA |
| 5 femA-SE | CCCATCTCTGCTG GCTTCTTT | CCGCATAGCTCCC TGCAA | CGCTGGTGGAACT TCAAATCGTTA TCG |

Forward primer A1 corresponds to SEQ ID No. 1. Reverse primer B1 corresponds to SEQ ID No. 2. Probe C1 corresponds to SEQ ID No. 3. Forward primer A4 corresponds to SEQ ID No. 10. Reverse primer B4 corresponds to SEQ ID No. 11. Probe C4 corresponds to SEQ ID No. 12. Forward primer A5 corresponds to SEQ ID No. 13. Reverse primer B5 corresponds to SEQ ID No. 14. Probe C5 corresponds to SEQ ID No. 15.

The final volume of the PCR mixture was 25 µl and contained the following compounds:

Reaction buffer 2×: 12.5 µl (commercialized by Eurogentec)
A1: 100 nM, B1: 100nM and C1: 75 nM
A4: 50 nM, B4: 50 nM and C4: 50 nM
A5: 400 nM, B5: 400 nM and C5: 100 nM
10 µl of the sample and the amplification run was immediately performed.

Fluorescent dyes linked to the probes were the following:
C1 (mecA) 5'-JOE and 3'-DABCYL
C4 (femA-SA) 5'-FAM and 3'-DABCYL
C5 (femA-SE) 5'-Texas Red® and 3'-DABCYL B. Amplification Conditions:

The assay has been developed according to Applied Biosystems specifications, except that 50 cycles were used to increase the sensitivity (without loss of specificity).

| | |
|---|---|
| incubation 1 → | 2 min. at 50° C. |
| incubation 2 → | 10 min. at 95° C. |
| incubation 3 → | 15 sec. at 95° C. |
| incubation 4 → | 1 min. at 60° C. |

(3 and 4 were repeated 50 times)

C. Analysis

After visual inspection of the data, the background for each fluorescent reporter was determined as the average fluorescence value measured during cycles 3-12. After background subtraction, the threshold value for each fluorescent reporter was calculated as 6-12 times preferably 8 times) the standard deviation of the background. A similar calculation was performed for femA-SE. Ct for femA-SE was determined using 100 pg DNA/well from control MRSE strain (isolate from a nasal swab) under the same conditions as described in A and B. The threshold value for mecA was then adjusted so that Ct for mecA =Ct for femA-SA. This determination was performed using 100 pg DNA/well from control MRSA strain (ATCC33591) under the same conditions as described in A and B. From screenshots obtained for femA-SA, mecA and femA-SE the smallest Ct among triplicates for each DNA target sequence was determined. MRSA was present when all following conditions were met:
1) Smallest Ct for mecA<40
2) Smallest Ct for femA-SA<40
3) Ct for mecA−Ct for femA-SE<0
MRSA was absent in all other conditions.

Example 8

For comparison purpose, the same samples as used in example 7 were analyzed in parallel using primers and probes of Example 2 section A (Table 1) as well as primers and probes of Example 7 section A (Table 2).

Results using primers and probes of Example 2:

| | Ct femA-SA | Ct mecA | Ct femA-SE |
|---|---|---|---|
| MRSA | 31.5 | 31.5 | 50 |
| MSSA | 32 | 50 | 50 |
| MRSE | 50 | 30 | 30 |
| MSSE | 50 | 50 | 28.6 |

Results using primers and probes of Example 7:

| | Ct femA-SA | Ct mecA | Ct femA-SE |
|---|---|---|---|
| MRSA | 27 | 27 | 50 |
| MSSA | 27.5 | 50 | 50 |
| MRSE | 50 | 26 | 26 |
| MSSE | 50 | 50 | 26 |

Primers and probes used in Example 7 provided similar interpretation but offered increased sensitivity, i.e. smaller Ct values for all three analyzed target genes.

Example 9

Example 9 was carried out as example 7 except that 1 pg of genomic DNA from the MSSA strain ATCC25923 was added as an internal control to the reaction buffer. After amplification, the analysis was performed on the basis of the Ct obtained for mecA and the Ct for femA-SE. Different spiked quantities ranging from 100 pg to 1 pg were tested and confirmed the linearity of the determination within this range of concentrations, Cts for femA-SA were 24 and 30-31, respectively. Detection and analysis were performed on either the ABI Prism Sequence Detection Systems (Applied Biosystems) or the Smart Cycler® (Cepheid).
Both provided similar linear results The presence and amount of MRSA was indicated when the difference between Ct for mecA−Ct for femA-SE<0. MRSA was absent in all other conditions. Taking advantage of 1 pg of spiked genomic DNA from MSSA, the Ct for femA-SA was measured to confirm that the amplification worked properly.

The invention claimed is:

1. A method for the detection and quantification of methicillin-resistant *Staphylococcus aureus* from a specimen comprising:
   a) contacting the specimen with Anti-Protein A antibodies so as to adsorb methicillin-resistant *Staphylococcus aureus* and/or methicillin-sensitive *Staphyloccoccus aureus*,
   b) separating said antibodies to which methicillin-resistant *Staphylococcus aureus* and/or methicillin-sensitive *Staphylococcus aureus* have been adsorbed from the specimen,
   c) lysing the methicillin-resistant *Staphylococcus aureus* and/or methicillin-sensitive *Staphylococcus aureus* adsorbed to said antibodies so as to release their DNA,
   d) preparing a solution comprising the released DNA and:
      i) a first pair of primers, which are capable, in an amplification reaction, of generating a first product, which is a portion of the mecA gene of methicillin-resistant *Staphylococcus aureus* or of methicillin-resistant *Staphylococcus* epidermidis;
      ii) a second pair of primers, which are capable, in an amplification reaction, of generating a second product, which is a portion of the genome of methicillin-resistant *Staphylococcus aureus* that does not include any of the mecA gene; and
      iii) a third pair of primers, which are capable, in an amplification reaction, of generating a third product, which is a portion of the genome of methicillin-resistant *Staphylococcus* epidermidis that does not include any of the mecA gene, wherein the second product and the third product have a homology of lower than 90% and do not cross-hybridize under conditions of 62° C. at 6 mM salt;
   e) subjecting the solution of step (d) to conditions for said amplification reaction;
   f) determining the amounts of the first product, the second product and the third product resulting from the amplification reaction.

2. The method of claim 1, wherein the adsorbed methicillin-resistant *Staphylococcus aureus* and/or methicillin-sensitive *Staphylococcus aureus* are lysed by applying shear forces.

3. The method of claim 1, wherein the second product is a portion of the femA gene of methicillin-resistant *Staphylococcus aureus*.

4. The method of claim 1, wherein the third product is a portion of the femA gene of methicillin-resistant *Staphylococcus* epidermidis.

5. The method of claim 1, wherein the first pair of primers are SEQ ID NO: 1 and SEQ ID NO: 2.

6. The method of claim 3, wherein the second pair of primers are SEQ ID NO: 4 and SEQ ID NO: 5.

7. The method of claim 3, wherein the second pair of primers are SEQ ID NO: 10 and SEQ ID NO: 11.

8. The method of claim 4, wherein the third pair of primers are SEQ ID NO: 7 and SEQ ID NO: 8.

9. The method of claim 4, wherein the third pair of primers are SEQ ID NO: 13 and SEQ ID NO: 14.

10. The method of claim 1, wherein the solution of step (d) further comprises a nucleic acid probe capable of binding to the first product during the amplification reaction.

11. The method of claim 1, wherein the solution of step (d) further comprises a nucleic acid probe capable of binding to the second product during the amplification reaction.

12. The method of claim 1, wherein the solution of step (d) further comprises a nucleic acid probe capable of binding to the third product during the amplification reaction.

13. The method of claim 1, wherein the amounts of the first product, the second product and the third product are determined by real-time PCR.

14. The method of claim 13, wherein the amount of methicillin-resistant *Staphylococcus aureus* is determined by detecting the cycle threshold of the first product, the second product and the third product, and determining the difference of the cycle thresholds obtained for the first product and obtained for the third product.

15. The method of claim 14, wherein:
   the smallest cycle threshold for the first product is less than 40
   the smallest cycle threshold for the second product is less than 40
   the difference between the cycle threshold of the first product and the cycle threshold of the third product is equal to or less than 0.

16. The method of claim 14, wherein the cycle threshold is set by determining the background of reach fluorescent dye used in the real-time PCR, as the average fluorescence value measured during 3-18 cycles.

17. The method of claim 1, wherein the solution of step d) further comprises an internal control.

18. The method of claim 17, wherein the internal control is a portion of the genome of methicillin-sensitive *Staphylococcus aureus* that does not include any of the mecA gene.

19. The method of claim 17, wherein the internal control is a portion of the femA gene of methicillin-sensitive *Staphylococcus aureus*.

20. The method of claim 17, wherein the amount of methicillin-resistant *Staphylococcus aureus* is determined by detecting the cycle threshold of the first product, the second product and the third product, and determining the difference of the cycle thresholds obtained for the first product and obtained for the third product.

21. The method of claim 20, wherein:

the smallest cycle threshold for the first product is less than 40 the smallest cycle threshold for the second product is less than 40 the difference between the cycle threshold of the first product and the cycle threshold of the third product is less than 0.

22. The method of claim 1, wherein the second pair of primers contain >3 mismatches to the third pair of primers in order to discriminate the second product from the third product.

23. The method of claim 1, wherein the first product, the second product and the third product resulting from the amplification reaction consist of approximately 100 ±50 nucleotides.

24. The method of claim 10, wherein the nucleic acid probe capable of binding to the first product during the amplification reaction is SEQ ID NO: 3.

25. The method of claim 11, wherein the nucleic acid probe capable of binding to the second product during the amplification reaction is SEQ ID NO: 6 or SEQ ID NO: 12.

26. The method of claim 12, wherein the nucleic acid probe capable of binding to the third product during the amplification reaction is SEQ ID NO: 9 and SEQ ID NO: 15.

* * * * *